(12) United States Patent
Hicks et al.

(10) Patent No.: US 8,969,599 B2
(45) Date of Patent: Mar. 3, 2015

(54) CERIUM-CONTAINING ZEOLITES AND COKE REDUCTION METHODS

(71) Applicants: Jason Christopher Hicks, Granger, IN (US); Gregory Thomas Neumann, Roseland, IN (US)

(72) Inventors: Jason Christopher Hicks, Granger, IN (US); Gregory Thomas Neumann, Roseland, IN (US)

(73) Assignee: University of Notre Dame du Lac, Notre Dame, IN (US)

( * ) Notice: Subject to any disclaimer, the term of this patent is extended or adjusted under 35 U.S.C. 154(b) by 0 days.

(21) Appl. No.: 14/203,253

(22) Filed: Mar. 10, 2014

(65) Prior Publication Data

US 2014/0256967 A1 Sep. 11, 2014

Related U.S. Application Data

(60) Provisional application No. 61/851,503, filed on Mar. 8, 2013.

(51) Int. Cl.
  *C07D 307/36* (2006.01)
  *B01J 29/40* (2006.01)
  *C07C 45/60* (2006.01)

(52) U.S. Cl.
  CPC ............... *B01J 29/405* (2013.01); *C07C 45/60* (2013.01); *C07D 307/36* (2013.01)
  USPC ........................................................ 549/505

(58) Field of Classification Search
  CPC .............................. B01J 29/405; C07D 307/36
  USPC ........................................................ 549/505
  See application file for complete search history.

(56) References Cited

U.S. PATENT DOCUMENTS

| 8,535,629 B2 | 9/2013 | Ballinger et al. |
| 8,557,730 B2 | 10/2013 | Burba et al. |
| 2012/0142520 A1 | 6/2012 | Bartek et al. |

FOREIGN PATENT DOCUMENTS

CA          1052365 A1    4/1974

OTHER PUBLICATIONS

French et al., "Catalytic pyrolysis of biomass for biofuels production", Fuel Processing Technology 91: 25-32 (2010).
Inaba et al., "Hydrogen Production by Gasification of Cellulose over Ni Catalysts Supported on Zeolites", Energy & Fuels 20: 432-438 (2006).
Murkute et al., "Supported mesoporous solid base catalysts for condensation of carboxylic acids", Journal of Catalysis 278: 189-199 (2011).
Pattiya, "Fast pryrolysis of cassava rhizome in the presence of catalysts", J. Anal. Appl. Pyrolysis 81: 72-79 (2008).
Pattiya, "Evaluation of catalytic pyrolysis of cassava rhizome by principal component analysis", Fuel 89: 244-253 (2010).
Van Kooten et al, "Hydrothermal deactivation of Ce-ZSM-5, Ce-beta, Ce-mordenite and Ce—Y zeolite deNOx catalysts", Catalysis Letters 63: 227-231 (1999).
Zhang et al., "Hydrothermal Stability of Cerium Modified Cu-ZSM-5 Catalyst for Nitric Oxide Decomposition", Journal of Catalysis 164, 131-145 (1996).

*Primary Examiner* — Taofiq A Solola
(74) *Attorney, Agent, or Firm* — Haukaas Fish PLLC; Michael H. Haukaas

(57) ABSTRACT

The invention provides a catalyst system for catalytic fast pyrolysis comprising a cerium-incorporated HZSM-5 zeolite (Catalyst 1), and methods of making and using the same. The invention also provides a process for reducing coke formation during catalytic fast pyrolysis of biomass using HZSM-5, wherein the process can include incorporating cerium into the HZSM-5 zeolite to produce Catalyst 1 prior to the catalytic fast pyrolysis.

20 Claims, 10 Drawing Sheets

A

B

CERIUM-CONTAINING ZEOLITES AND COKE REDUCTION METHODS

RELATED APPLICATIONS

This application claims priority under 35 U.S.C. §119(e) to U.S. Provisional Patent Application No. 61/851,503, filed Mar. 8, 2013, which is incorporated herein by reference.

BACKGROUND OF THE INVENTION

Technological advancements for efficient and economical production of energy and fuels from more sustainable resources than fossil fuels is an important goal for scientists and engineers. Biomass is well known as an abundant potential source of fuels and specialty chemicals. When biomass materials are subjected to thermal treatment, such as in pyrolysis processes, the liquids/vapors generated comprise oxygenated molecules, which are directly released from the biomass as it is thermally decomposed. Other polynuclear aromatic molecules can be formed from cross-interactions of the nascent molecules at the biomass/vapor interface and in the vapor phase. It is known that large biomass particles as well as long residence times enhance these side reactions and the fuel oil products produced contain larger molecules at a given thermolysis operating reactor temperature. To that effect, the operating parameters need to be optimized for a given kind of biomass material to minimum liquid hydrocarbon oxygen content, obtain the maximum oil yield, and minimum gas and coke yields.

Petroleum-based resources are currently a primary source of chemicals and transportation fuels. However, because of various factors including the finite reserves of petroleum, their unequal geographic distributions, and the environmentally motivated desire to decrease $CO_2$ emissions, renewable energy sources, such as lignocellulosic biomass, have become promising candidates for the production of renewable fuels and chemicals. To use these abundant resources effectively with existing infrastructure, these highly oxygenated feedstocks must be chemically converted into products that are more stable and more similar to currently used fuels and chemicals. Catalytic fast pyrolysis is a thermochemical method that has been studied as potentially scalable process to convert solid biomass feedstocks into high energy density liquids or chemical platform molecules. It has been shown that the addition of a catalyst in a pyrolysis reactor enhances control over the product distribution through selective conversion of the vapor phase products into hydrocarbon products. It has been found that HZSM-5 has a high selectivity to aromatics and a gasoline range hydrocarbon, but is not selective for the production of oxygenated chemicals. Furthermore, large quantities of water and coke are typically observed with the use of HZSM-5 resulting in its own deactivation.

Accordingly, there is a need for an improved method for converting biomass into more useful chemicals. There is also a need for improved zeolite catalysts that generate less during catalytic fast pyrolysis of biomass.

SUMMARY OF THE INVENTION

One aspect of the invention provides a catalyst system for catalytic fast pyrolysis comprising a cerium-incorporated high silica zeolite, such as a cerium-incorporated HZSM-5 zeolite (Catalyst 1). The cerium-incorporated high silica zeolite can include silicon and aluminum with a Si/Al ratio ranges from about 10 to about 300; cerium ranging from about 0.30 wt % to about 2.5 wt % of said zeolite; optionally water; and a catalyst matrix having a mesopore size ranging from about 20 angstroms to about 500 angstroms (about 2 nm to about 50 nm).

Another aspect of the invention provides a composition comprising Catalyst 1 prepared by the steps of (1) preparing a dry gel of Si, Al, $H_2O$, and Ce, and then (2) crystallizing the dry gel by steam assisted crystallization to form the Catalyst 1.

Another aspect of the invention relates to a method of incorporating cerium into HZSM-5 to produce Catalyst 1 comprising: 1) preparing a dry gel of Si, Al, $H_2O$, and Ce, and then (2) crystallizing the dry gel by steam assisted crystallization to form Catalyst 1.

Another aspect of the invention relates to a process for the conversion biomass by catalytic fast pyrolysis, the process comprising heating the biomass to a conversion temperature in presence of the catalyst system for catalytic fast pyrolysis according the first aspect of the invention described above.

Another aspect of the invention relates to a process for reducing coke formation during catalytic fast pyrolysis of biomass using HZSM-5, wherein the process comprises incorporating cerium into the HZSM-5 zeolite to produce Catalyst 1 prior to the catalytic fast pyrolysis.

Further aspects and embodiment of the invention will follow from the discussion that follows below.

BRIEF DESCRIPTION OF THE DRAWINGS

The following drawings form part of the specification and are included to further demonstrate certain embodiments or various aspects of the invention. In some instances, embodiments of the invention can be best understood by referring to the accompanying drawings in combination with the detailed description presented herein. The description and accompanying drawings may highlight a certain specific example, or a certain aspect of the invention. However, one skilled in the art will understand that portions of the example or aspect may be used in combination with other examples or aspects of the invention.

DETAILED DESCRIPTION

Figure 1:
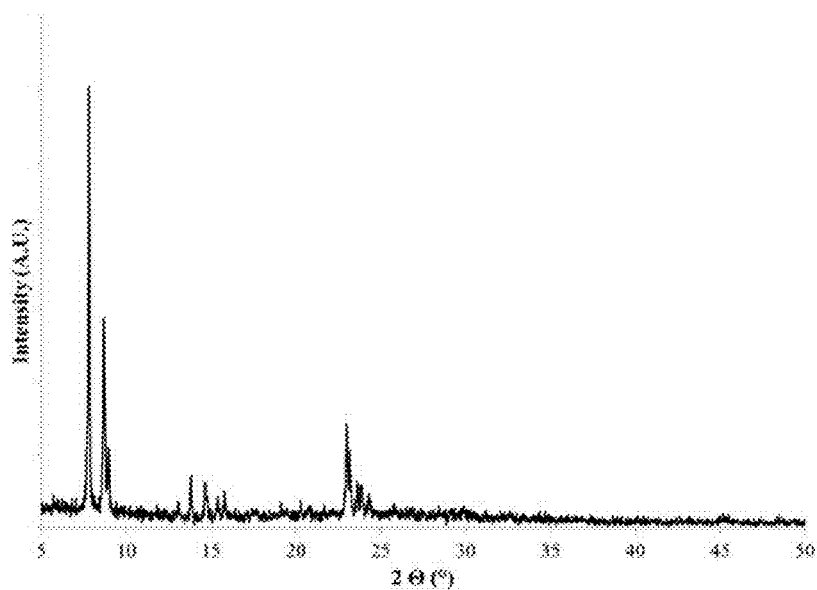
FIG. 1 depicts the powder XRD pattern of Catalyst 2.
Figure 2:
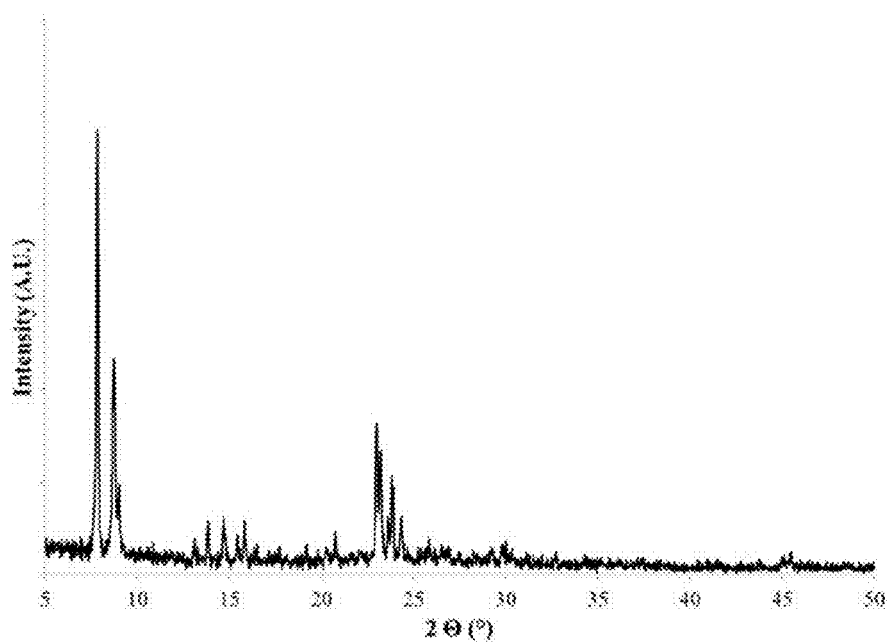
FIG. 2 depicts the powder XRD pattern of Catalyst 1.
Figure 3:
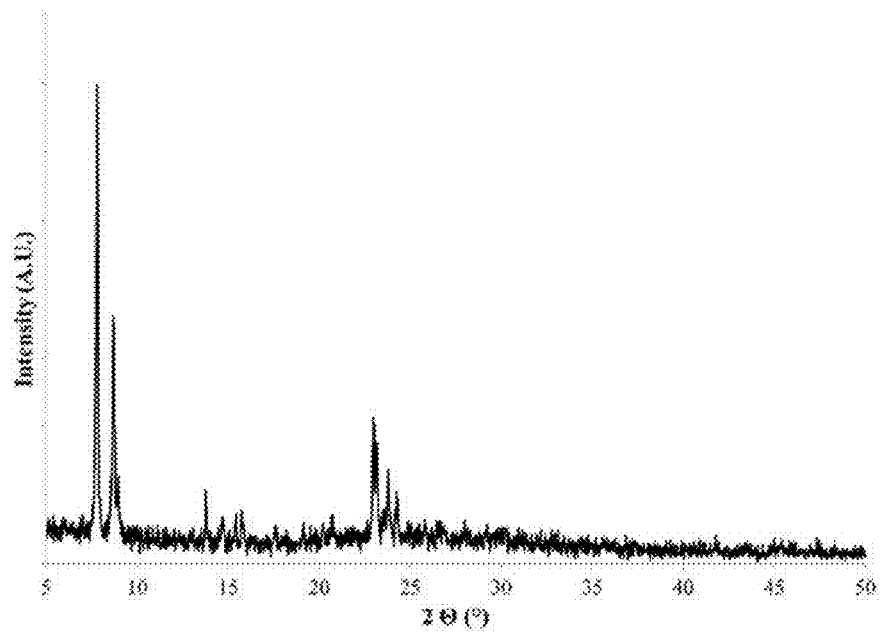
FIG. 3 depicts the powder XRD pattern of Catalyst 3.
Figure 4:
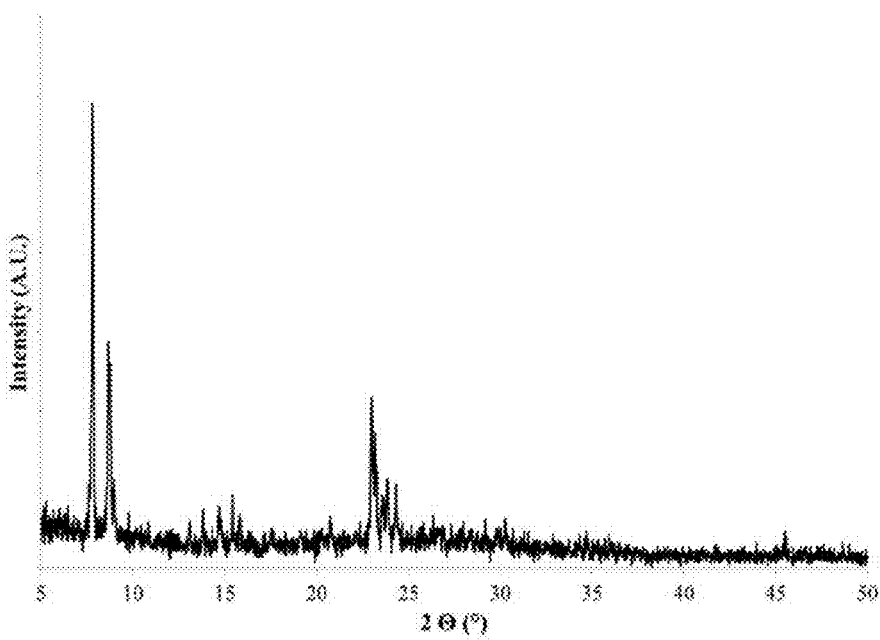
FIG. 4 depicts the powder XRD pattern of Catalyst 4.
Figure 5:
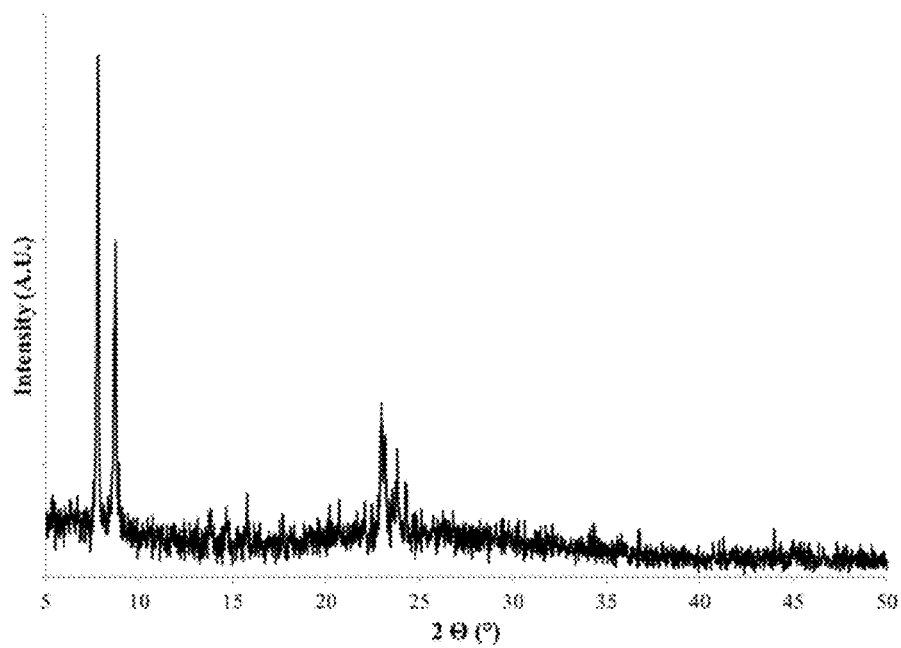
FIG. 5 depicts the powder XRD pattern of Catalyst 5.
Figure 6:
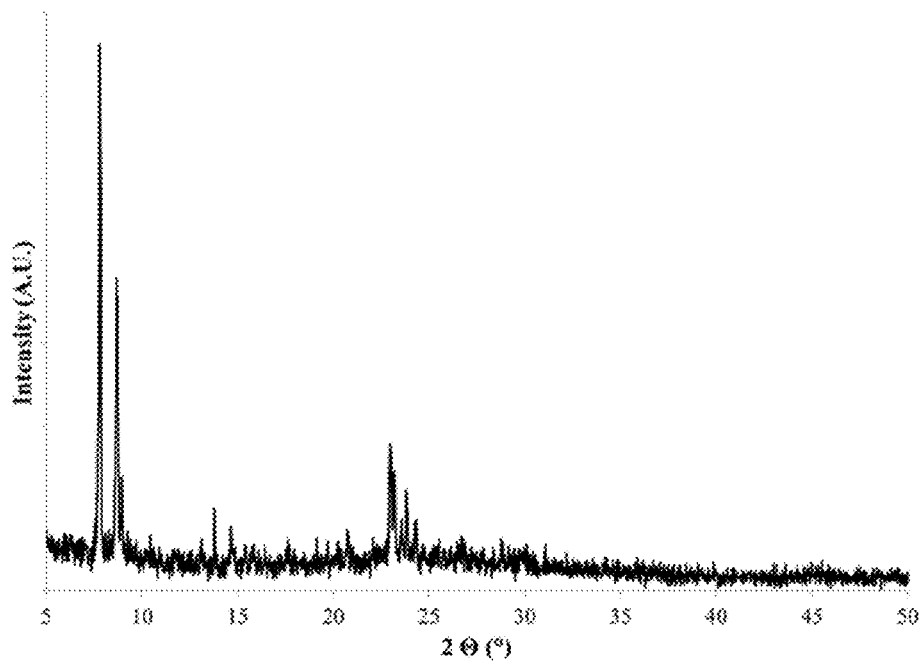
FIG. 6 depicts the powder XRD pattern of regenerated Catalyst 1.
Figure 7:
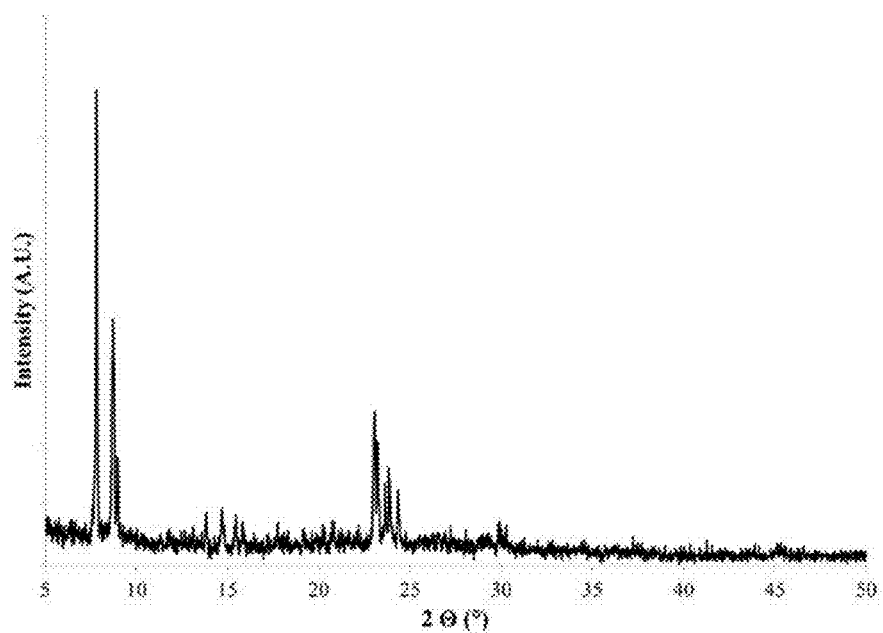
FIG. 7 depicts the powder XRD pattern of post TGA of Catalyst 1.

The incorporation of cerium into HZSM-5 is a novel feature applicable to all aspects of this invention, and this incorporation of cerium into HZSM-5 provides several key advantages over HZSM-5 without cerium incorporated. These advantages include (1) an increased capability of Catalyst 1 to convert highly oxygenated biomass during catalytic fast pyrolysis and (2) less coking of Catalyst 1 compared to HZSM-5 that results in Catalyst 1 staying active for a longer period of time during biomass conversion. More specifically, the Catalyst 1 shifts the selectivity from typical HZSM-5 products (benzene, toluene, and xylenes) to valuable oxygenated chemicals (furans, ketones, and aldehydes) during the catalytic fast pyrolysis of lignocellulosic biomass. In addition, the novel Catalyst 1 catalyst produces less coke (about 40 wt % or 11 mol %) and an increased CO production through decarbonylation reactions, and all of these improved properties of the novel Catalyst 1 catalyst persisted after catalyst regeneration and recycle.

Definitions

The following definitions are included to provide a clear and consistent understanding of the specification and claims. As used herein, the recited terms have the following meanings. All other terms and phrases used in this specification have their ordinary meanings as one of skill in the art would understand. Such ordinary meanings may be obtained by reference to technical dictionaries, such as *Hawley's Condensed Chemical Dictionary* $14^{th}$ Edition, by R. J. Lewis, John Wiley & Sons, New York, N.Y., 2001.

References in the specification to "one embodiment", "an embodiment", etc., indicate that the embodiment described may include a particular aspect, feature, structure, moiety, or characteristic, but not every embodiment necessarily includes that aspect, feature, structure, moiety, or characteristic. Moreover, such phrases may, but do not necessarily, refer to the same embodiment referred to in other portions of the specification. Further, when a particular aspect, feature, structure, moiety, or characteristic is described in connection with an embodiment, it is within the knowledge of one skilled in the art to affect or connect such aspect, feature, structure, moiety, or characteristic with other embodiments, whether or not explicitly described.

The singular forms "a," "an," and "the" include plural reference unless the context clearly dictates otherwise. Thus, for example, a reference to "a substance" includes a plurality of such "substances", so that a substance X includes a plurality of substances X. It is further noted that the claims may be drafted to exclude any optional element. As such, this statement is intended to serve as antecedent basis for the use of exclusive terminology, such as "solely," "only," and the like, in connection with any element described herein, and/or the recitation of claim elements or use of "negative" limitations.

The term "and/or" means any one of the items, any combination of the items, or all of the items with which this term is associated. The phrase "one or more" is readily understood by one of skill in the art, particularly when read in context of its usage.

The term "about" can refer to a variation of ±5%, ±10%, ±20%, or ±25% of the value specified. For example, "about 50" percent can in some embodiments carry a variation from 45 to 55 percent. For integer ranges, the term "about" can include one or two integers greater than and/or less than a recited integer at each end of the range. Unless indicated otherwise herein, the term "about" is intended to include values, e.g., weight percentages, proximate to the recited range that are equivalent in terms of the functionality of the individual ingredient, the composition, or the embodiment. The term about can also modify the end-points of a recited range as discuss above in this paragraph.

As will be understood by the skilled artisan, all numbers, including those expressing quantities of ingredients, properties such as molecular weight, reaction conditions, and so forth, are approximations and are understood as being optionally modified in all instances by the term "about." These values can vary depending upon the desired properties sought to be obtained by those skilled in the art utilizing the teachings of the descriptions herein. It is also understood that such values inherently contain variability necessarily resulting from the standard deviations found in their respective testing measurements.

As will be understood by one skilled in the art, for any and all purposes, particularly in terms of providing a written description, all ranges recited herein also encompass any and all possible sub-ranges and combinations of sub-ranges thereof, as well as the individual values making up the range, particularly integer values. A recited range (e.g., weight percentages or carbon groups) includes each specific value, integer, decimal, or identity within the range. Any listed range can be easily recognized as sufficiently describing and enabling the same range being broken down into at least equal halves, thirds, quarters, fifths, or tenths. As a non-limiting example, each range discussed herein can be readily broken down into a lower third, middle third and upper third, etc. As will also be understood by one skilled in the art, all language such as "up to", "at least", "greater than", "less than", "more than", "or more", and the like, include the number recited and such terms refer to ranges that can be subsequently broken down into sub-ranges as discussed above. In the same manner, all ratios recited herein also include all sub-ratios falling within the broader ratio. Accordingly, specific values recited for radicals, substituents, and ranges, are for illustration only; they do not exclude other defined values or other values within defined ranges for radicals and substituents.

One skilled in the art will also readily recognize that where members are grouped together in a common manner, such as in a Markush group, the invention encompasses not only the entire group listed as a whole, but each member of the group individually and all possible subgroups of the main group. Additionally, for all purposes, the invention encompasses not only the main group, but also the main group absent one or more of the group members. The invention therefore envisages the explicit exclusion of any one or more of members of a recited group. Accordingly, provisos may apply to any of the disclosed categories or embodiments whereby any one or more of the recited elements, species, or embodiments, may be excluded from such categories or embodiments, for example, for use in an explicit negative limitation.

The term "contacting" refers to the act of touching, making contact, or of bringing to immediate or close proximity, including at the molecular level, for example, to bring about a chemical reaction, or a physical change, e.g., in a mixture, in a reaction mixture.

An "effective amount" refers to an amount effective to bring about a recited effect, such as an amount necessary to form products in a reaction mixture. Determination of an effective amount is typically within the capacity of persons skilled in the art, especially in light of the detailed disclosure provided herein. The term "effective amount" is intended to include an amount of a compound or reagent described herein, or an amount of a combination of compounds or reagents described herein, e.g., that is effective to form products in a reaction mixture. Thus, an "effective amount" generally means an amount that provides the desired effect.

As used herein, "substantially" refers to greater that about 50% of the amount referred to, wherein the amount referred to relates any unit of measurement such as weight amount, a ratio, angstroms, or any other unit of measurement that the term substantially is referring to. Substantially can also refer to greater that 75% of an amount that is referred to. Substantially can also refer to greater than 90%, of an amount that is referred to. Substantially can also refer to greater than about 95% of an amount that is referred to.

The term "biomass" refers organic matter, such as plant matter, that can be converted to fuel and is therefore regarded as a potential energy source. A non-limiting example of biomass is lignocellulosic biomass.

The term "fast pyrolysis" or "biomass fast pyrolysis" as used herein refers to a process that converts solid biomass into highly oxygenated liquids, char and light gasses at high temperatures of greater than about 450° C. in the absence of oxygen.

The term "zeolite" refers to a microporous, aluminosilicate mineral that is commonly used as commercial adsorbents and catalysts.

The term ZSM-5 refers a zeolite with a high silica to alumina ratio. The substitution of an aluminum ion (charge 3+) for a silicon ion (charge 4+) requires the additional presence of a proton, which gives the zeolite a high level of acidity and which causes its activity. ZSM-5 is a very porous material and throughout its structure it has an intersecting two-dimensional pore structure. ZSM-5 has two types of pores, and both types are formed by 10-membered oxygen rings. One of these pores is straight and elliptical in cross section, and the second pores intersect the straight pores at right angles, in a zig-zag pattern and are circular in cross section.

The term "mesopore" refers to a material containing pores with diameters from about 2 nm to about 50 nm.

The term "micropore" refers to a material containing pores with diameters of less than about 2 nm.

Pluronic® P-123 is the tradename for a triblock copolymer, and the nominal chemical formula is $HO(CH_2CH_2O)_{20}(CH_2CH(CH_3)O)_{70}(CH_2CH_2O)_{20}H$.

Pluronic® F-127 (also known as Poloxamer 407) is a triblock copolymer consisting of a central hydrophobic block of polypropylene glycol flanked by two hydrophilic blocks of polyethylene glycol. The approximate lengths of the two PEG blocks is about 101 repeat units and the approximate length of the propylene glycol block is about 56 (e.g., 50-60) repeat units.

Aspects and Embodiments of the Invention

The following aspects and embodiments of the invention are exemplary, and all equivalents thereof are intended to be included within the scope of this invention.

One aspect of the invention relates to a catalyst system for catalytic fast pyrolysis comprising a cerium-incorporated high silica zeolite, wherein the cerium-incorporated high silica zeolite comprises:
a) silicon and aluminum with a Si/Al ratio ranges from about 10 to about 300;
b) cerium ranging from about 0.30 wt % to about 2.5 wt % of said zeolite;
c) $H_2O$; and
d) a catalyst matrix having a mesopore size ranging from about 20 angstroms to about 500 angstroms.

In other embodiments of this catalyst system, the Si/Al ratio is 10:1. In another embodiment of this catalyst system, the Si/Al ratio is 15:1. In another embodiment of this catalyst system, the Si/Al ratio is 20:1. In another embodiment of this catalyst system, the zeolite is Catalyst 1, ZSM-11, ZSM-12, or SSZ-24. In another embodiment of this catalyst system, the zeolite is Catalyst 1. In other embodiments of this catalyst system, the catalyst matrix has a mesopore size ranging from about 60 angstroms to about 200 angstroms; the wt % of cerium ranges from about 0.5 wt % to about 2.0 wt %; and; the Si/Al ratio ranges from about 40 to about 280.

In another embodiment, the catalyst system for catalytic fast pyrolysis comprises a cerium-incorporated HZSM-5 zeolite (Catalyst 1), wherein the cerium-incorporated HZSM-5 zeolite comprises:
a) silicon and aluminum with a Si/Al ratio ranges from about 20 to about 300;
b) cerium ranging from about 0.30 wt % to about 2.5 wt % of said zeolite;
c) $H_2O$; and
d) a catalyst matrix having a mesopore size ranging from about 20 angstroms to about 500 angstroms.

In another embodiment of this aspect of the invention, the cerium-incorporated HZSM-5 zeolite has catalyst matrix with a mesopore size ranging from 60 angstroms to 200 angstroms. In still yet another embodiment of this aspect of the invention, the cerium-incorporated HZSM-5 zeolite has a catalyst matrix with a mesopore size of about 110 angstroms. For purposes of clarification, it is known that ZSM-5 has a micropore (as opposed to mesopore) size of 5.6 angstroms.

Another embodiment of the catalyst system for catalytic fast pyrolysis comprises the cerium-incorporated HZSM-5 zeolite, wherein the wt % of cerium ranges about 0.5 wt % to about 2.0 wt %. In another embodiment of this aspect of the invention, the wt % of cerium in the cerium-incorporated HZSM-5 zeolite ranges from about 0.5 wt % to about 1.0 wt %. In another embodiment of this aspect of the invention, the wt % of cerium in the cerium-incorporated HZSM-5 zeolite is about 1.9 wt %. In another embodiment of this aspect of the invention, the wt % of cerium in the cerium-incorporated HZSM-5 zeolite is about 0.7 wt %.

Another embodiment of the catalyst system for catalytic fast pyrolysis comprises the cerium-incorporated HZSM-5 zeolite (Catalyst 1), wherein the Si/Al ratio ranges from about 20 to about 300. In another embodiment of this aspect of the invention, Si/Al ratio in the cerium-incorporated HZSM-5 zeolite ranges from about 40 to about 280. In another embodiment of this aspect of the invention, Si/Al ratio in the cerium-incorporated HZSM-5 zeolite ranges from about 40 to about 200. In another embodiment of this aspect of the invention, Si/Al ratio in the cerium-incorporated HZSM-5 zeolite ranges from about 50 to about 100. In another embodiment of this aspect of the invention, Si/Al ratio in the cerium-incorporated HZSM-5 zeolite ranges from about 50 to about 70. In another embodiment of this aspect of the invention, Si/Al ratio in the cerium-incorporated HZSM-5 zeolite ranges from about 50 to about 60. In another embodiment of this aspect of the invention, Si/Al ratio in the cerium-incorporated HZSM-5 zeolite is about 55.

Another aspect of the invention relates to a composition comprising Catalyst 1 prepared by the steps of (1) preparing a dry gel of Si, Al, $H_2O$, and Ce, and then (2) crystallizing the dry gel by steam assisted crystallization to form the Catalyst 1. In another embodiment of this aspect of the invention, the dry gel is prepared by first combining Pluronic® F-127 or Pluronic® P-123 with de-ionized water at about 40° C. for about 1 hour; followed by the step of adding in the aluminum, silicon and cerium sources at about 40° C. for about 1 hour; followed by the step of adding a structure directing agent, tetrapropylammonium hydroxide and mixing the resulting mixture in a reaction vessel for about 24 hours at about 40° C.; followed by the step of aging the mixture at about 60° C. for about 16 hours; followed by the step of exposing the reaction vessel to the atmosphere and raising the temperature of the mixture to about 90° C. to dry the mixture for at least 16 hours until a solid dry gel is formed In another embodiment of this aspect of the invention, Pluronic® F-127 is used in the dry gel preparation described above.

In another embodiment of this aspect of the invention, Pluronic® P-123 is used in the dry gel preparation described above. In another embodiment of this aspect of the invention, the dry gel is steamed for about 18 hours at about 175° C. to form a powder; followed by step of washing and filtering the powder; followed by the step of calcining the powder at about 550° C. for about 4 hours. In another embodiment of this aspect of the invention, the source of aluminum is aluminum isopropoxide. In another embodiment of this aspect of the invention, the source of the silicon is tetraethyl orthosilicate. In another embodiment of this aspect of the invention, the source of the cerium is cerium nitrate hexahydrate. In another embodiment of this aspect of the invention, the source of aluminum is aluminum isopropoxide; the source of the silicon is tetraethyl orthosilicate; and the source of the cerium is cerium nitrate hexahydrate, cerium acetate, or cerium chloride. In another embodiment of this aspect of the invention, the source of the cerium is cerium nitrate hexahydrate. In another embodiment of this aspect of the invention, the source of the cerium is cerium acetate. In another embodiment of this aspect of the invention, the source of the cerium is cerium chloride. In another embodiment of this aspect of the invention, the sources used are about 0.20 g of aluminum isopropoxide; about 10.4 g of tetraethyl orthosilicate; and about 0.141 g of cerium nitrate hexahydrate, or substantially equivalent amounts of each of these sources; and the Si:Al:$H_2$O:Ce ratio is about 4.99:0.079:200:0.0325, or substantially equivalent ratios thereof.

Another aspect of the invention relates to a method of incorporating cerium into HZSM-5 to produce Catalyst 1 comprising: 1) preparing a dry gel of Si, Al, $H_2$O, and Ce, and then (2) crystallizing the dry gel by steam assisted crystallization to form Catalyst 1. In another embodiment of this aspect of the invention, the dry gel is prepared by combining Pluronic® F-127 and de-ionized water at about 40° C. for about 1 hour; followed by the step of stirring in the aluminum, silicon and cerium sources at about 40° C. for about 1 hour; followed by the step of adding a structure directing agent, tetrapropylammonium hydroxide and mixing the resulting mixture in a reaction vessel for about 24 hours at about 40° C.; followed by the step of aging the mixture at about 60° C. for about 16 hours; followed by the step of exposing the reaction vessel to the atmosphere and raising the temperature to about 90° C. to dry the mixture for at least about 16 hours until a dry solid gel is formed. In another embodiment of this aspect of the invention, the dry gel is steamed for about 18 hours at about 175° C. to form a powder; followed by step of washing and filtering the powder; followed by the step of calcining the powder at about 550° C. for about 4 hours.

In another embodiment of this aspect of the invention, the source of aluminum is aluminum isopropoxide; the source of the silicon is tetraethyl orthosilicate; and the source of the cerium is cerium nitrate hexahydrate, cerium acetate or cerium chloride. In another embodiment of this aspect of the invention, the source of the cerium is cerium nitrate hexahydrate. In another embodiment of this aspect of the invention, the source of the cerium is cerium acetate. In another embodiment of this aspect of the invention, the source of the cerium is cerium chloride. In another embodiment of this aspect of the invention, the sources used are about 0.20 g of aluminum isopropoxide; about 10.4 g of tetraethyl orthosilicate; and about 0.141 g of cerium nitrate hexahydrate, or substantially equivalent amounts thereof; and the Si:Al:$H_2$O:Ce ratio is about 4.99:0.079:200:0.0325.52, or substantially equivalent ratios thereof.

Another aspect of the invention relates to a process for the conversion biomass by catalytic fast pyrolysis, the process comprising heating the biomass to a conversion temperature in presence of the catalyst system for catalytic fast pyrolysis according the first aspect of the invention described above. All of embodiments of the catalyst system for catalytic fast pyrolysis described above are meant to be included as separate embodiments of this process for the conversion biomass by catalytic fast pyrolysis.

In another embodiment of the process for the conversion biomass by catalytic fast pyrolysis, the conversion temperature ranges from about 500° C. to about 700° C. In another embodiment of the process for the conversion biomass by catalytic fast pyrolysis, the conversion temperature ranges from about 550° C. to about 650° C. In another embodiment of the process for the conversion biomass by catalytic fast pyrolysis, the conversion temperature is about 600° C. In another embodiment of the process for the conversion biomass by catalytic fast pyrolysis, the biomass is an oxygenated biomass feedstock. In another embodiment of the process for the conversion biomass by catalytic fast pyrolysis, the catalyst system selectively converts highly oxygenated biomass. In another embodiment of the process for the conversion biomass by catalytic fast pyrolysis, the highly oxygenated biomass is converted to organic compounds comprising furan, methylfuran, acetone and acetaldehyde. In another embodiment of the process for the conversion biomass by catalytic fast pyrolysis, the process of converting biomass includes the ketonization of carboxylic acid compounds.

Another aspect of the invention relates to a process for reducing coke formation during catalytic fast pyrolysis of biomass using HZSM-5, wherein the process comprises incorporating cerium into the HZSM-5 zeolite to produce Catalyst 1 prior to the catalytic fast pyrolysis. All of embodiments of the catalyst system for catalytic fast pyrolysis described above are meant to be included as separate embodiments of this process for reducing coke formation during catalytic fast pyrolysis of biomass using HZSM-5. In another embodiment of this aspect, the wt % of coke reduction using Catalyst 1 compared to HZSM-5 is 40 wt %.

The cerium of each embodiment described herein can be exchanged with lanthanum using a corresponding lanthanum compound in the zeolite preparation.

The following Examples are intended to illustrate the above invention and should not be construed as to narrow its scope. One skilled in the art will readily recognize that the Examples suggest many other ways in which the invention could be practiced. It should be understood that numerous variations and modifications may be made while remaining within the scope of the invention.

EXAMPLES

In the following Examples, the following chemicals were commercially available: cerium (III) nitrate hexahydrate (from Sigma), poly(ethyleneglycol)-block-poly(propylene glycol)-block-poly(ethyleneglycol) (Pluronic®-F 127, from Aldrich), tetraethylorthosilicate (TEOS, Alpha Aesar), cerium (III) nitrate hexahydrate (from Sigma), aluminum isopropoxide (from Sigma), tetrapropyl ammonium hydroxide (from Alpha Aesar), glucose (from Acros), and deionized water (DI water). Zeolyst BV5524 was calcined for about 4 hours at 550° C. to obtain the protonated form designated as Catalyst 3. Silicon, cerium, and aluminum ICP standards (BDH, ARISTAR) were used for ICP analysis. Benzene (from Sigma), toluene (from Sigma), p-xylene (from Sigma), furan (from Alfa Aesar), methyl-furan (from Alfa Aesar), acetone (from Sigma), acetaldehyde (from Alfa Aesar), furfural (from Sigma), acetic acid (from Sigma), naphthalene (from Sigma), methylnapthalene (from Sigma), 30% carbon monoxide in helium (CO, from Praxair), carbon dioxide ($CO_2$, from Praxair), 10% methane in helium ($CH_4$, from Praxair), 10% ethane in helium ($C_2H_6$, from Praxair), 10% propane in helium ($C_3H_8$, from Praxair), and 3% ammonia in helium ($NH_3$, from Praxair) were obtained from commercial sources and were used as received for GC/MS external standards and TCD calibrations.

Example 1

Synthesis of Catalyst 1

Materials were synthesized using a modified procedure described by Shi et al. (Direct Synthetic Strategy of mesoporous ZSM-5 Zeolites by Using Conventional Block Copolymer Templates and the Improved Catalytic Properties. *ACS Catalysis* 2011, 1(4), 287-291), wherein the modification of the procedure included the addition of a cerium source, which was $CeNO_3 6H_2O$. In the synthesis, 3.2 g of the template, Pluronic® F-127, was stirred in 36.0 g of DI water at a temperature of about 40° C. until a clear mixture was obtained. After about an hour, the silicon, aluminum, and cerium sources were stirred in the mixture at 40° C. respectively. The sources used were 10.4 g tetraethyl orthosilicate, 0.20 g aluminum isopropoxide, and 0.141 g cerium nitrate hexahydrate. The $Si:Al:H_2O:Ce$ ratio in the composition was 499:0.0979:200:0.0325. After about one hour of mixing, the pH of the mixture was 6.51. 3.8 g of the structure directing agent, tetrapropylammonium hydroxide was then added drop wise to the mixture. This mixture was then stirred for about 24 hours at 40° C. The stirring was then stopped and the mixture was aged at 60° C. for 16 hours. Finally the mixture was uncapped and the temperature was raised to 90° C. to dry the mixture overnight. In order to crystallize the dry mixture the dry gel was added to Teflon sleeves in order to perform the SAC method. The solid gel was contained in a glass vial and water was added around the vial so that liquid water would not be in contact with the dry gel. The Teflon sleeve was placed in a stainless steel reactor vessel as the next step. For the steaming, the ratio used was 1.5 g of dry gel to 0.5 g of DI water. The dry gel was steamed for about 18 hours at 175° C. The resultant product was then washed, filtered, and then the resulting powder was calcined at 550° C. for about 4 hours.

Example 2

Synthesis of Catalyst 2

The synthetic procedure for Meso-HZSM-5 was, including the amounts used, was identical to Catalyst 1 except no cerium was added. The pH was measured at 9.15 without the addition of a cerium source.

Example 3

Synthesis of Incipient Wetness Catalyst 4

Calcined Meso-ZSM-5 was dried overnight in a vacuum oven at about 60° C. 0.0717 g of cerium nitrate was then dissolved in 1.0041 g of DI water. This mixture was then added dropwise to the dry material in a ratio of 1 g Ce mixture/1 g Catalyst 2. The wet material was then dried and calcined at 550° C. for 4 hours.

Example 4

Synthesis of Exchanged Conventional ZSM-5 Catalyst 5

Prior to calcination, 1 g of the ammonium form of commercial ZSM-5 was stirred in a 1 M aqueous mixture of cerium nitrate. This exchange was carried out three times at 80° C. The material was then dried and calcined at 550° C. for 4 hours.

Example 5

Catalytic Fast Pyrolysis

Catalytic fast pyrolysis procedures were conducted using a model 5200 pyroprobe analytical pyrolizer (CDS Analytical). The probe was a resistively heated platinum coil that holds a quartz tube filled with reactant and catalyst. The catalysts and biomass model compound were premixed to a homogenous mixture of about 9:1, and then the quartz tube was filled. All procedures were run with 10 mg of mixture being charged in the quartz tube. The solid was contained within the open ended quartz tube with a plug of quartz wool on either side of the mixture.

Pyrolysis was carried out using helium as the inert carrier gas. The carrier gas stream was plumbed to the injection side of an Agilent model 7890 gas chromatograph (GC) interfaced with a 5975 Hewlett Packard mass spectrometer (MS). The probe temperature was set to about 600° C. with a ramp rate of about 1000° C./s and held for about 360 seconds. During the fast pyrolysis, the vapors were carried to the GC/MS with helium as the inert gas for pyrolysis and the carrier gas for the GC/MS system. A constant flow of 0.5 mL min 1 was programmed. The temperature of the column was held at about 50° C. for 3 minutes and then the temperature was increased to 200° C. at a rate of 10° C. $min^{-1}$. The temperature was then held at 200° C. for about 15 minutes. The GC injector temperature was set to about 275° C. and the transfer line from the pyrolizer to the GC was set to about 300° C. The products were quantified using external standard calibrations. Calibration curves for these procedures were constructed by varying the concentration of pure chemical standards. For accurate analysis of the products, three columns were used. A HP-5MS column was used to quantify furfural and xylenes. A VF-624 ms column was used to quantify the remaining liquid products. A GS-Carbon Plot column was used to quantify the gas phase products, CO,$CO_2$, ethane, propane, and methane. Propane and ethane calibration curves were used to quantify propene and ethylene respectively. All of the samples in this procedure were run at least 3 times on the three columns to determine the product distribution.

Calculations. The molar carbon yields were calculated using the molar carbon ratio. The yield was calculated as follows:

Yield=mol product/mol carbon in product/mol glucose/mol carbon in glucose

The liquid selectivities were calculated as:

Liquid Selectivity %=mol carbon of product/total mol carbon in liquid.

Material Characterization. XRD patterns were collected on a Bruker, D8 Advanced powder Xray diffractometer with the use of Cu Kα radiation. The powder catalysts were crushed and dispersed in acetone and then were pipetted onto a glass slide for analysis. The pattern was then collected from a 2 θ angle of 5 to 50 varied at 0.02°/step and held at about 0.75 sec for each angle. $N_2$ isotherms were then collected on a Quantachrome NOVA 2200 after all materials were degassed at about 130° C. overnight. DeBoer parameters were used for the t-plot method as well as the BJH method. A JASCO model V-670 UV-Vis spectrometer was used for UV-Vis diffuse reflectance analysis. The catalysts were finely crushed and then placed in an analysis cell. The wavelength was varied from about 200 to about 800 nm in the diffuse reflection mode.

FT IR measurements were conducted with a Bruker Tensor 27 in DRIFTS mode. First, a background was collected using finely crushed and dried KBr. Next, catalysts were mixed with dry KBr, and the sample was scanned from about 400 to about 4000 $cm^{-1}$. The surface oxidation states were determined using a Kratos model XSAM800 X-ray photoelectron spectrometer. Catalysts were dispersed on carbon tape and pumped down to ultra-high vacuum (~$10^{-8}$ torr). For cerium, a survey scan was first performed, and this was followed by 35 scans at 60 s/scan. The scans were done in the range of 925 to 875 eV. Data acquisition was performed using Kratos' Vision 2 software. Data analysis was performed using CasaXPS version 2.3.15. A Magellan 400 field emission scanning electron microscope (SEM) was employed to image the catalyst.

Catalysts were finely crushed and were dispersed on carbon tape and then were next plasma cleaned for about 2 minutes. After the plasma cleaning step, 2.8 nm of iridium was sputtered onto the catalyst surface to increase the contrast in the image. The Si/Al ratio was determined using an energy dispersive X-ray spectrometer QUANTAX 200A attachment.

A Perkin Elmer Optima 3300XL ICP-OES was employed to determine the weight percent of cerium in each sample. Dissolved catalyst mixtures were analyzed three times to determine the average signal. Using external standards of cerium, a calibration with an $R^2$ value of about 0.999 was constructed for the determination of the weight percent of cerium in each of the unknowns injected.

A Mettler Toledo TGA/DSC I STAR System was used in order to determine any coke that remained on spent catalysts. The remaining coke was determined by measuring the weight loss between about 250 and about 800° C. The temperature was ramped from about 25° C. to about 800° C. at a rate of about 15° C./min in air to combust the organics. The acidity of the catalysts was measured with ammonia temperature programmed desorption (TPD) by using a Micromeritics Chemisorb 2750. The catalysts were prepared by ramping the temperature to about 120° C. at a rate of about 10° C./min in pure helium. After holding the temperature at about 120° C. for about 1 hour, the temperature was ramped to about 200° C. and held for about 2 hours using the same ramp rate in helium. After holding for about 2 hours, the temperature was allowed to fall to about 120° C. and a 2% ammonia gas in helium was allowed to flow over the catalysts for about 3 hours. The gas was then switched back to pure helium.

After about an hour of flow, the thermal conductivity was analyzed as the temperature was ramped to about 600° C. to desorb the ammonia. The area under the curve was then calculated, and the volume chemisorbed to the material was calculated using a calibration of ammonia gas. The peaks were then fit using Gaussian shaped curves with aid of the TPX software.

Physical and Chemical Properties of Catalyst 1 and Other Catalysts. The new material (Catalyst 1) was compared with four other materials to determine how cerium incorporation affects catalytic properties in the catalytic fast pyrolysis of glucose (1) commercial H-ZSM-5 (HZSM-5C), (2) mesoporous HZSMS (Catalyst 2), (3) cerium added by incipient wetness (Catalyst 4), and (4) cerium added via ion exchanged (Catalyst 5). These studies were described by the inventor in Hicks et al, *ACS Catal.* 2012, 2, 642-646, the contents of which are incorporated by reference in its entirety.

TABLE 1

Physical and Chemical Properties of Studied Catalysts.

| material | wt % Ce | Si/Al | $S_{BET}$ ($m^2/g$) | $V_{micro}^d$ ($cm^3/g$) | $S_{mirco}^d$ ($m^2/g$) | $S_{external}^d$ ($m^2/g$) | mesopore size (Å) |
|---|---|---|---|---|---|---|---|
| Catalyst 1 | 1.92 | 55 | 351 | 0.136 | 268 | 83.3 | 110 |
| Catalyst 2 | 0 | 49 | 378 | 0.146 | 289 | 88.5 | 155 |
| Catalyst 3 | 0 | 25 | 392 | 0.167 | 329 | 63.4 | — |
| Catalyst 4 | 2.75 | 49 | 198 | 0.07 | 134 | 64.0 | 111 |
| Catalyst 5 | 1.05 | 50 | 279 | 0.118 | 230 | 49.1 | — | a. ICP-OES
b. from vendor
c. EDXS
$^d$t-plot method
e. BJH desorption

Figure 8:
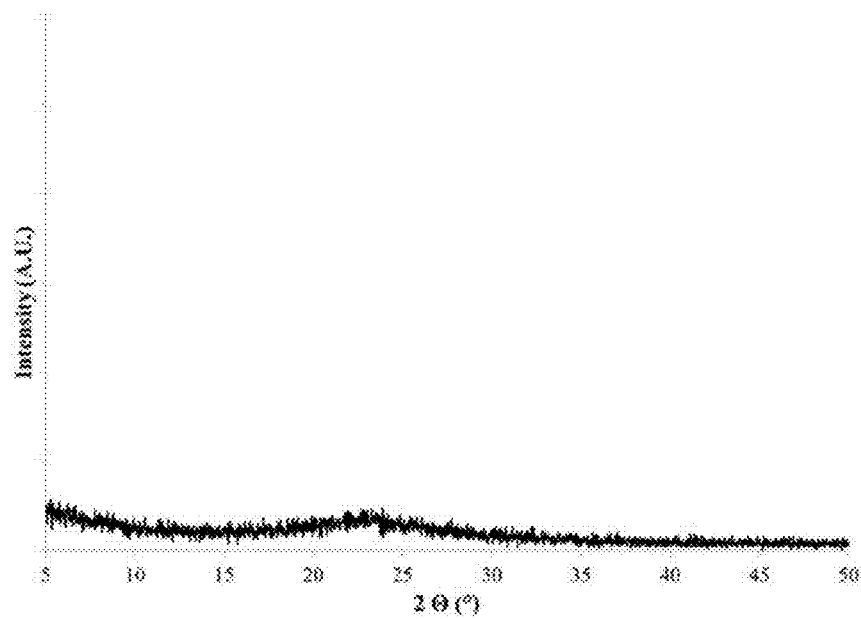
FIG. 8 depicts the powder XRD pattern of pre-steamed Catalyst 1.

X-ray diffraction (XRD) was performed on Catalyst 1 before and after the steaming step. The steaming step was necessary to crystallize the catalysts synthesized by the dry gel method (FIG. 8).

The XRD patterns (FIGS. 1-7) show characteristic peaks for an MFI type zeolite at 20 angles of ~8° and 23°. 2 The amount of cerium incorporated in Catalyst 1 was determined by ICP-OES (Table 1). The amount of cerium added to the initial mixture led to a theoretical incorporation of 2.25 wt % Ce, but the synthesized material had an actual loading of about 1.92 wt % Ce. Accordingly, about 85% of the cerium added to the precursor mixture was retained in the final material. Nitrogen physisorption was used to determine pore diameter (Barret-Joyner-Halenda (BJH) method), surface areas (Brunauer-Emmett-Teller (BET) method), and pore volumes (t-plot method) of the catalysts.

As shown in Table 1, Catalyst 1 had mesopores with pore diameters of ~110 Å. The micropore volume of this material was calculated to be ~0.136 cc/g by the t-plot method which was similar to the non-cerium containing mesoporous catalyst (Catalyst 2), and this is typical for HZSM-5.

Figure 9:
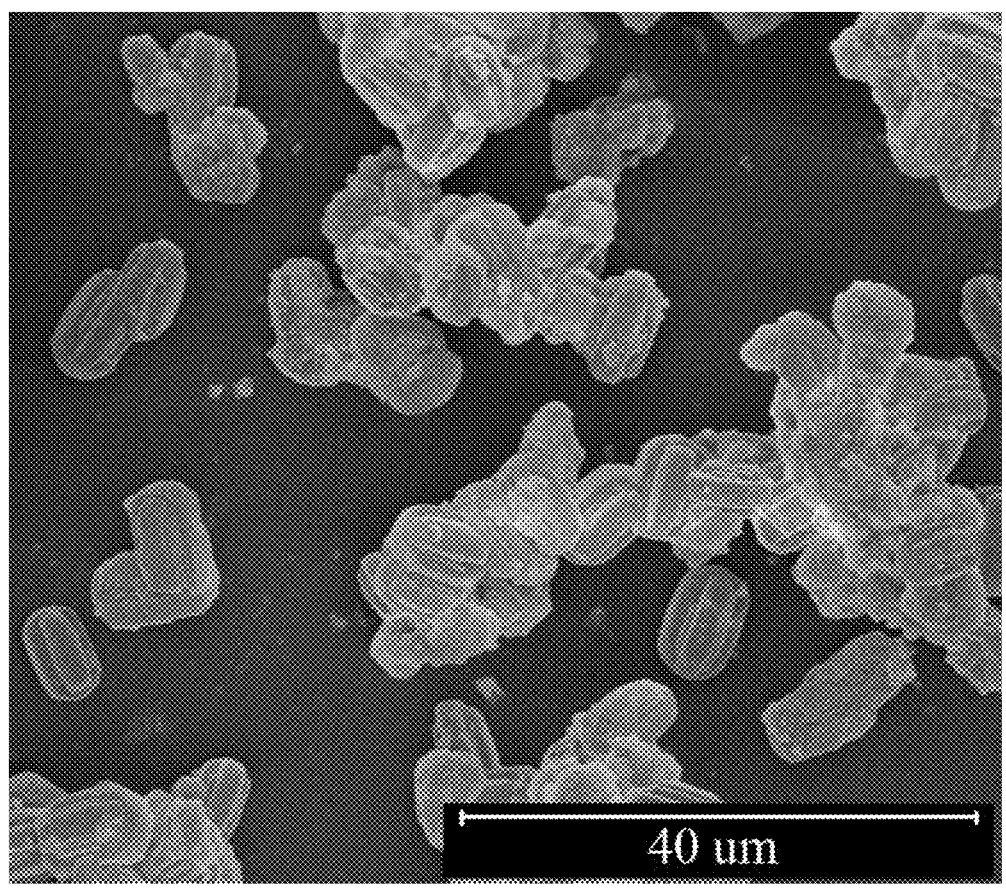
FIG. 9 depicts an SEM image of Catalyst 1.
Figure 10:
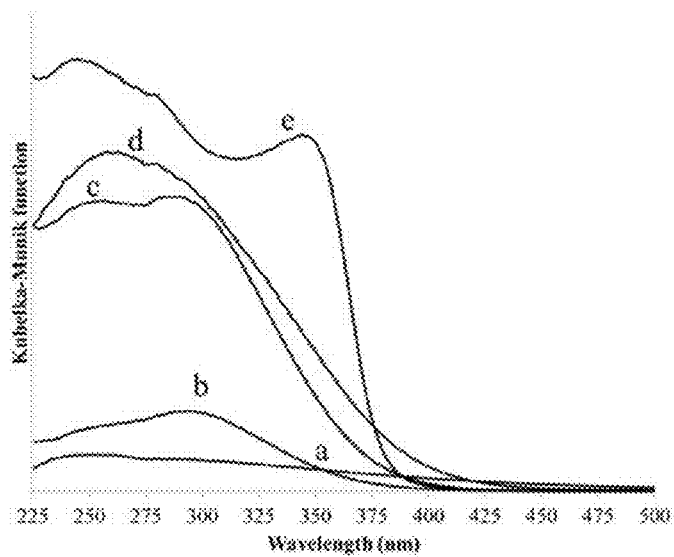
FIGS. 10 (A and B) depict diffuse reflectance UV-Vis spectra and IR spectra comparing various catalysts.
Figure 10:
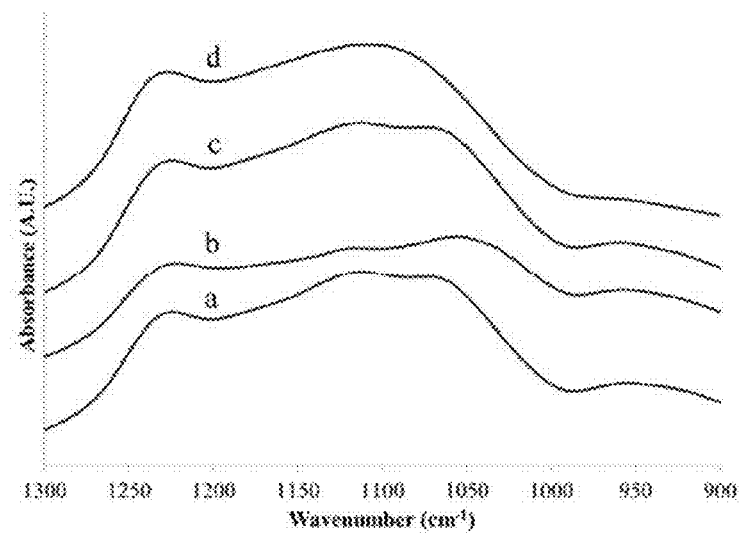

SEM of Catalyst 1 (FIG. 9) shows particles possessing a twinned prism-like morphology with a non-smooth surface and particle size of 9 μm. Diffuse reflectance UV-Vis was used to probe whether the incorporated cerium in Catalyst 1 was extra-framework or intraframework. Bulk $CeO_2$ (FIG. 10A(e)) showed a large absorption band at ~370 nm. The Catalyst 2 material (FIG. 10A(a)) shows very low absorbance because of the absence of cerium. The Catalyst 1 material shows a strong absorption at 260 nm, and this is assigned to the charge transfer of $O^{2-}$ to $Ce^{3+}$, indicating the incorporation of cerium into the framework. The UV-Vis spectra of the cerium nitrate triple-exchanged commercial ZSM-5 (Catalyst 5) with a cerium loading of about 1.05 wt % and the incipient wetness (Catalyst 4) with a cerium loading of about 2.75 wt % control materials (FIG. 10A (b) and (c), respectively) show peaks shifted toward lower energies, which correspond to extra-framework cerium bulk phases. Although there is a strong peak at 260 nm in the Catalyst 1, it is possible that both intra-framework and extra-framework cerium species are present due to the broadness of the large absorption band.

Figure 11:
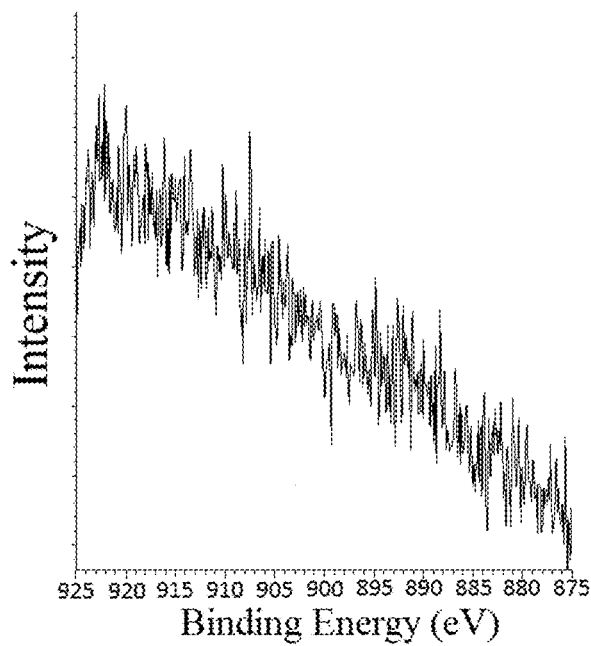
FIG. 11 depicts the X-ray photoelectron spectroscopy spectra of A) Catalyst 2 and B) Catalyst 1.
Figure 11:
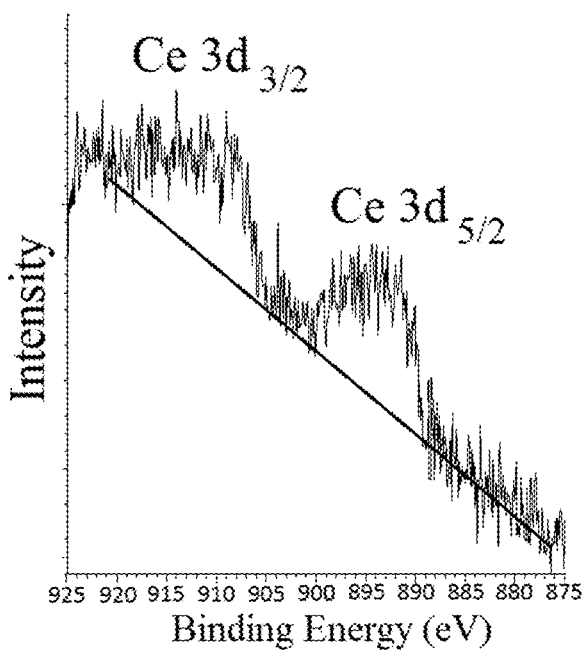

Diffuse reflectance FT-IR spectra (FIG. 10B) were obtained for Catalyst 2, Catalyst 1, Catalyst 4, and Catalyst 5. Because the vibrations of Si-0 and Si-0-Ce both appear at the same wavenumber, 970 cm$^{-1}$, this absorbance band cannot definitively indicate that there was intra-framework cerium incorporation. The absorbance band about 1070 cm$^{-1}$ was assigned to the u,(Si-0-Si). A shift of 15 wave numbers to 1055 cm$^{-1}$ was noticed in the spectrum of Catalyst 1 (FIG. 10B(b)), which is characteristic of the incorporation of cerium into the framework. When cerium was added to the control catalysts (FIG. 10 B(c) and (d)), this shift was not observed. Finally, X-ray photoelectron spectroscopy (XPS) was used to probe the oxidation state of the surface cerium present on Catalyst 1. The XPS results (FIG. 11) show two binding energies at 864 and 913 eV.

Figure 12:
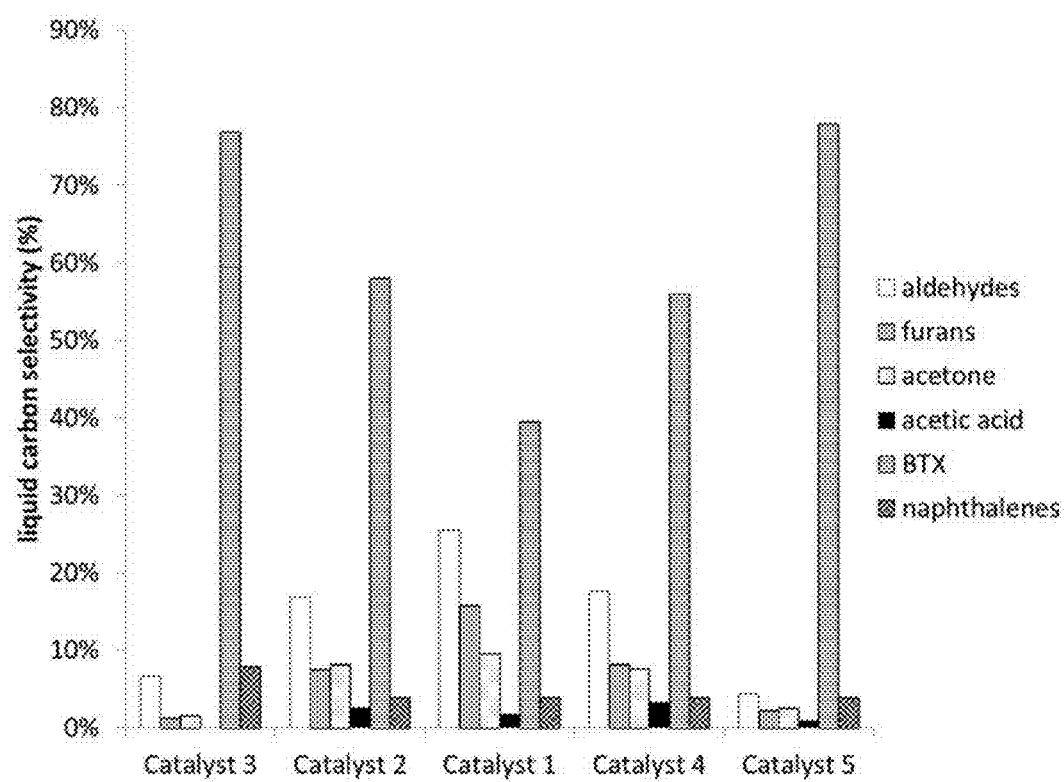
FIG. 12 depicts the molar carbon selectivity of catalytic fast pyrolysis of glucose comparing various catalysts. Key: Aldehydes: acetaldehyde, furfural. Furans: furan, methyl-furan. BTX: benzene, toluene, xylenes. Naphthalenes: naphthalene, methyl-naphthalene.

Catalytic fast pyrolysis of glucose was studied at about 600° C. in a Pyroprobe 5200 reactor. All of the Catalysts in Table 1 were studied in this reactor with a feed to catalyst ratio of 1:9, a 1000°/s ramp rate, and a 360 s residence time. The primary products from the pyrolysis of glucose with Catalyst 3 were toluene, benzene, xylenes, and naphthalenes (FIG. 12 and Table 2). Using Catalyst 5, the aromatic carbon selectivities were determined to be unaffected. The Catalyst 2 catalyst (without cerium) also produced aromatics, but the selectivities to oxygenated chemicals increased.

TABLE 2

Summary of the Molar Carbon Yields and Liquid Selectivity of Catalytic Fast Pyrolysis of Glucose with Various Catalysts.

| Catalyst | Catalyst 3 | Catalyst 2 | Catalyst 1 | Catalyst 4 | Catalyst 5 |
|---|---|---|---|---|---|
| Overall Carbon Yield % | | | | | |
| aromatics | 24.1 | 21.3 | 11.3 | 13.0 | 28.8 |
| oxygenates | 2.4 | 11.5 | 12.3 | 7.4 | 3.3 |
| CO | 18.7 | 16.0 | 21.8 | 22.4 | 18.6 |
| $CO_2$ | 9.6 | 3.8 | 5.1 | 5.9 | 4.9 |
| light gases | 2.9 | 3.0 | 3.6 | 3.8 | 1.2 |
| coke | 43.8 | 42.0 | 39.2 | 45.4 | 42.9 |
| total | 101.6 | 97.6 | 93.2 | 98.0 | 99.7 |
| Liquid Carbon Selectivity | | | | | |
| acetaldehyde | 6.7 | 16.6 | 25.0 | 17.3 | 4.4 |
| furfural | 0.0 | 0.2 | 0.4 | 0.3 | 0.0 |

TABLE 2-continued

Summary of the Molar Carbon Yields and Liquid Selectivity of Catalytic Fast Pyrolysis of Glucose with Various Catalysts.

| Catalyst | Catalyst 3 | Catalyst 2 | Catalyst 1 | Catalyst 4 | Catalyst 5 |
|---|---|---|---|---|---|
| furan | 1.2 | 6.2 | 12.5 | 6.4 | 1.8 |
| methyl furan | 0.0 | 1.3 | 3.2 | 1.7 | 0.3 |
| acetone | 1.5 | 8.1 | 9.5 | 7.6 | 2.5 |
| acetic acid | 0.0 | 2.6 | 1.8 | 3.2 | 0.8 |
| benzene | 12.5 | 7.1 | 6.9 | 8.5 | 13.5 |
| toluene | 48.5 | 40.4 | 17.3 | 32.8 | 52.2 |
| xylenes | 15.7 | 10.4 | 15.2 | 14.6 | 1.1 |
| naphthalenes | 13.9 | 7.2 | 8.2 | 7.6 | 12.3 |

Catalyst 4 produced similar amounts of aromatics and oxygenated chemicals, without a noticeable effect due to cerium versus only the incorporation of mesoporosity. However, Catalyst 1 showed a surprising shift in selectivities to more oxygenated chemicals rather than aromatics (FIG. 12 and Table 2), and this was much greater than what was observed with mesopore incorporation alone. In addition, the overall acidity of Catalyst 1 decreased.

The intra-framework Ce catalyst (Catalyst 1) produced more acetone than all the other catalysts that were tested and less acetic acid than the other mesoporous catalysts. Since the ketonization of carboxylic acids has been well studied as a method to stabilize pyrolysis oils, the inventive catalyst's ability to upgrade acetic acid to acetone under reaction conditions was also studied. It was found that Catalyst 1 could ketonize acetic acid to form acetone in much higher percent yields (45.4%) than non-cerium containing Catalyst 2 (2.5%), Catalyst 5 (4.4%), and Catalyst 4 (6.4%). These results indicate that Catalyst 1 can improve bio-oils by converting carboxylic acids to more stable products via ketonization.

When using conventional HZSM-S catalysts, large coke production is regularly observed, which suggests the need for catalysts with greater carbon efficiencies. Hierarchical zeolites are believed to have better performance than conventional HZSM-5 by decreasing diffusion limitations, allowing larger molecules to both enter and escape the porous network more easily, thus improving a catalyst's resistance to coking. It was found that coke formation decreased significantly from 34 wt % using commercial HZSM-S(Catalyst 3) to 20 wt % with Catalyst 1 and decreased 11% by molar carbon yield (Table 2). In addition to catalyst coke reduction, an increase in decarbonylation reactions to form CO was observed with the Catalyst 1 catalyst.

Figure 13:
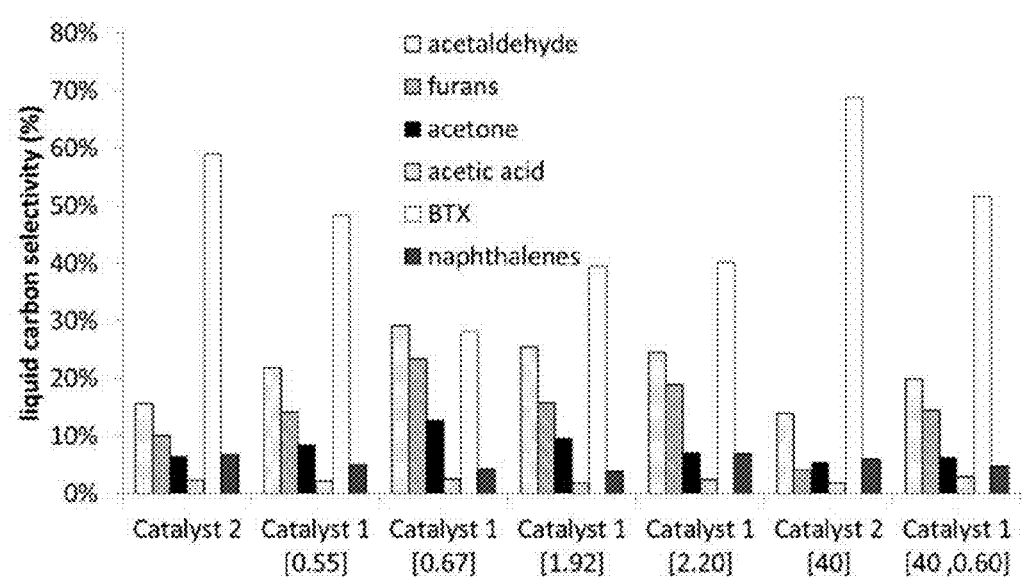
FIG. 13 depicts the liquid molar carbon selectivity of catalytic fast pyrolysis of glucose comparing various catalysts with different Si:Al ratios.

The regeneration and recyclability of these zeolite catalysis were studied. A large reduction in micropore volume after the first use has indicated that the coke that is formed is primarily located on the micropore surfaces. The used Catalyst 1 was regenerated at about 630° C. for 30 mm after a ramp of 2° C./mm. The $N_2$ physisoprtion data (Table 3) shows the removal of carbon deposits and the persistence of mesopores. After regenerating the catalyst, low catalyst coke formation during reaction was maintained (FIG. 13). After the catalyst was regenerated, the catalyst had showed a high selectivity to chemicals production from glucose.

TABLE 3

Fresh, Spent, and Regenerated Catalyst Physical Data.

| Material[a] | $S_{BET}$ (m²/g) | Pore Size (Å)[b] | $V_{micro}$[c] (cm³/g) | $S_{micro}$[c] (m²/g) | $S_{external}$[c] (m²/g) |
|---|---|---|---|---|---|
| Fresh Catalyst 1 | 351 | 110 | 0.136 | 268 | 83.3 |
| Coked Catalyst 1 | 264 | 195 | 0.099 | 193 | 71.3 |
| Regenerated Catalyst 1 | 310 | 201 | 0.121 | 236 | 74.1 |
| Post TGA Catalyst 1 | 245 | 206 | 0.098 | 189 | 55.5 |

[a]Catalyst 1.
[b]BJH Desorption.
[c]t-Plot Method

Accordingly, the synthesis of cerium-incorporated hierarchical HZSM-5 catalysts with the benefits of high selectivities to chemicals from biomass and low catalyst coking was achieved. Experimental evidence described herein demonstrates the presence of cerium incorporation in the framework and reduced acidity of these materials are responsible for the marked shift in selectivities and decrease in coke formation compared to commercial HZSM-5. Furthermore, the cerium-incorporated catalyst was capable of performing ketonization of carboxylic acids and thus stabilizing the resulting pyrolysis oil. These multifunctional catalysts maintained selectivities and activities upon regeneration and recycling.

The effect of cerium loading on catalyst reactivity was also investigated by the inventor as described in Hicks and coworkers, *Top. Catal.* (2012) 55:196-208, the contents of which are incorporated by reference in its entirety. The production of oxygenated chemicals increased with incorporation of cerium (FIG. 13).

With only 0.55 wt % cerium incorporated into Catalyst 1 [Si:Al ratio=50 and Cerium wt %=0.55], the selectivity to liquid oxygenates increased by over 15% compared to Catalyst 2 [Si:Al ratio=50]. It was also found that the carbon molar yield of CO increased by about 3%. With more cerium in the material, a further shift to oxygenated chemicals and increased CO production was observed with Catalyst 1 [Si:Al ratio=50 and Ce wt %=0.67]. It was found that more acetone was produced with the use of Catalyst 1. In addition to increased CO yield and increased selectivity to oxygenates, coke production was reduced with the addition of cerium to the materials in combination with Si:Al ratios of 50 and 40. The lowest coke production, highest oxygenated liquid production, and highest CO production was observed with Catalyst 1 [Si:Al ratio=50 and Ce wt %=0.67].

The high yield of CO obtained with all of the cerium-containing catalysts is thought to occur through decarbonylation reactions of intermediate aldehydes. This was supported by increased production of furans and CO with the use of Catalyst 1 catalysts compared to the Catalyst 2 material, since furfural, a common and abundant aldehyde found in pyrolysis oil, is known to undergo decarbonylation to produce CO and furan.

To investigate this proposed pathway, a series of experiments was run using catalysts with and without cerium. It was found that furfural reacted over Catalyst 1 under fast pyrolysis conditions to produce furan and CO with higher selectivities and yields than Catalyst 3, Catalyst 2, and Catalyst 4. This indicates cerium incorporated within the Catalyst 1 materials plays a more significant role in the decarbonylation of furfural compared to catalysts with cerium added via ion-exchange or incipient wetness. Carbonaceous deposition (Coke) analysis by thermogravimetric analysis (TGA) was used to determine the amount of carbonaceous material, referred to as coke, remaining on the catalyst after pyrolysis.

Figure 14:
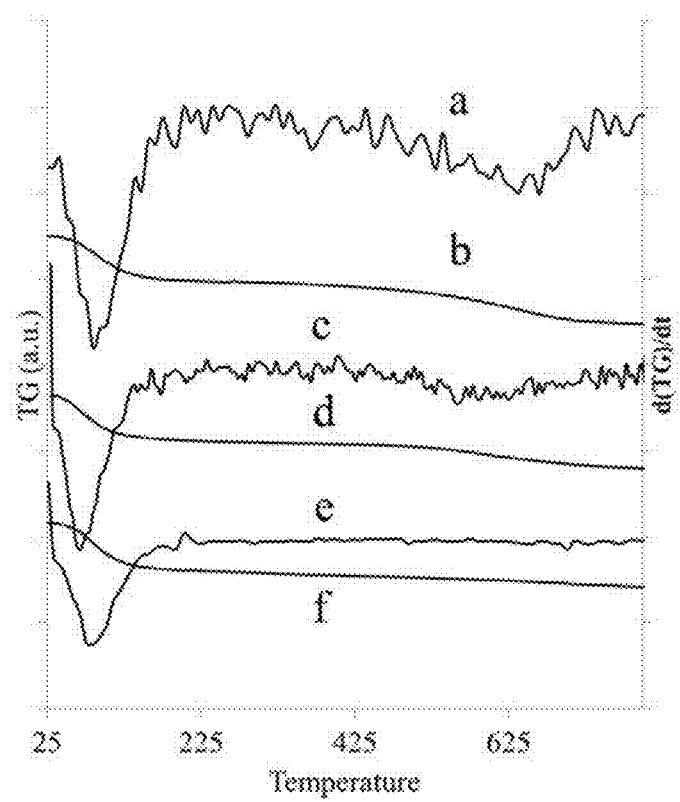
FIG. 14 depicts the thermogravimetric plot of cerium containing catalysts. Thermogravimetric plot with derivative a) d(TG)/dt of spent cerium containing catalyst; b) weight loss of spent cerium containing catalyst; c) d(TG)/dt of spent non cerium catalyst; d) weight loss of spent non cerium catalyst; e) d(TG)/dt of fresh catalyst; f) weight loss of fresh catalyst.

Three characteristic curves are shown in FIG. 14, with two clear stages of weight loss for the spent catalysts (FIG. 14 *a, c*). In general, there are three regions used to analyze coke using TGA. The first stage is in the temperature range of about 25 to about 180° C., where weight loss is attributed to volatile organics and water. The second stage (180-330° C.) was referred to as soft coke, and the third stage (330-700° C.) was referred to as hard coke. As shown in FIG. 14*f*, the fresh catalyst only showed weight loss in the first stage, which is most likely due to physisorbed water. The spent cerium containing catalysts were also observed to have significant weight loss during the first stage due to water or light organics remaining after pyrolysis. However, these catalysts also exhibited weight loss in the stage 3 region, which is characteristic of the combustion of hard coke. Comparing the spent catalysts with and without cerium, there was a noticeable difference in the combustion temperature of the coke on the catalysts. As shown in FIG. 14, coke on the cerium containing catalyst combusted at about 630° C. However, coke on the non-cerium containing catalyst (FIG. 14*d*) combusted at about 570° C. This shift to a higher combustion temperature is likely due to a higher percentage of carbon in the coke formed on cerium-containing catalysts (70% C with Ce and 65% C without Ce).

Multifunctional hierarchical HZSM-5 catalysts were synthesized with various aluminum and cerium concentrations as described by the inventor in Hicks et al, *Top Catal* (2012) 55:196-208, the contents of which are incorporated by reference in its entirety. The role of aluminum and cerium was investigated. For syntheses with low Si:Al ratios (15 and 20), amorphous materials were created. However, at Si:Al ratios of 30, 40, and 50, crystalline materials were synthesized with cerium incorporated within the catalyst. Catalysts with theoretical Si:Al ratios of 40 and 50, with and without cerium, were studied for the fast pyrolysis of glucose at about 600° C. It was found from these studies that with lower Si:Al ratios, selectivity to BTX had increased. With the addition of cerium. Catalyst 1 catalysts showed an increase in selectivity to CO production and oxygenated chemicals, and a decrease in coke formation. Furthermore, it was found that the cerium in Catalyst 1 catalysts aids in increased selective decarbonylation of furfural to form CO and furan compared to Catalyst 2 and commercial HZSM-5. These catalyst properties highlight their potential tunability to produce a variety of useful products while reducing coke formation.

Studies of catalytic fast pyrolysis at about 600° C. with Catalyst 1 of various Ce concentrations (expressed in Ce wt % below) and using glucose as the biomass precursor (Table 4). The following product ratios were observed:

TABLE 4

Product ratios based on Ce loading in Catalyst 1.

| | Carbon Molar Yield Ratios | | | |
|---|---|---|---|---|
| Ce wt % | Furan:BTX | Furan:Coke | Acetaldehyde:BTX | Acetaldehyde:Coke |
| 0.00% | 17.1% | 6.7% | 26.4% | 10.3% |
| 0.55% | 29.1% | 10.3% | 45.1% | 16.0% |
| 0.67% | 82.9% | 13.0% | 103.7% | 16.2% |
| 1.92% | 50.5% | 9.4% | 82.1% | 15.3% |
| 2.20% | 47.1% | 8.6% | 60.9% | 11.1% |

While specific embodiments have been described above with reference to the disclosed embodiments and examples, such embodiments are only illustrative and do not limit the scope of the invention. Changes and modifications can be made in accordance with ordinary skill in the art without departing from the invention in its broader aspects as defined in the following claims.

All publications, patents, and patent documents are incorporated by reference herein, as though individually incorporated by reference. No limitations inconsistent with this disclosure are to be understood therefrom. The invention has been described with reference to various specific and preferred embodiments and techniques. However, it should be understood that many variations and modifications may be made while remaining within the spirit and scope of the invention.

What is claimed is:

1. A catalyst system for catalytic fast pyrolysis comprising a cerium-incorporated high silica zeolite, wherein the cerium-incorporated high silica zeolite comprises:
   a) silicon and aluminum with a Si/Al ratio ranges from about 10 to about 300;
   b) cerium ranging from about 0.3 wt % to about 2.5 wt % of said zeolite;
   c) water; and
   d) a catalyst matrix having a mesopore size ranging from about 20 angstroms to about 500 angstroms.

2. The catalyst system according to claim 1 wherein the zeolite is Catalyst 1, ZSM-11, ZSM-12, or SSZ-24.

3. The catalyst system according to claim 1 wherein the zeolite is Catalyst 1.

4. The catalyst system according to claim 1 wherein catalyst matrix has a mesopore size ranging from about 60 angstroms to about 200 angstroms; the wt % of cerium ranges from about 0.5 wt % to about 2.0 wt %; and; the Si/Al ratio ranges from about 40 to about 280.

5. The catalyst system according to claim 1 wherein the catalyst matrix has mesopore size of about 100 angstroms to about 120 angstroms.

6. The catalyst system according to claim 1 wherein the wt % of cerium is about 0.7 wt %.

7. A composition comprising Catalyst 1, wherein Catalyst 1 is a catalyst as described in claim 1, prepared by the steps of (1) preparing a dry gel of Si, Al, $H_2O$, and Ce, and then (2) crystallizing the dry gel by steam assisted crystallization to form the Catalyst 1.

8. The composition comprising Catalyst 1 prepared by the process according to claim 7 wherein the dry gel is prepared by first combining Pluronic® F-127 or Pluronic® P-123 with de-ionized water at about 40° C.; followed by adding in the aluminum, silicon and cerium sources at about 40° C.; followed by adding a structure directing agent tetrapropylammonium hydroxide, and mixing the resulting mixture in a reaction vessel at about 40° C.; followed by aging the mixture at about 60° C. for at least about 8 hours; and followed by exposing the reaction vessel to the atmosphere and raising the temperature of the mixture to about 90° C. to dry the mixture for a period of time sufficient to form a solid dry gel.

9. The composition comprising Catalyst 1 according to claim 8 wherein the solid dry gel is steamed at about 175° C. to form a powder; followed washing and filtering the powder; and calcining the powder at about 500° C. to about 600° C.

10. The composition comprising Catalyst 1 prepared by the process according to claim 7 wherein the source of aluminum is aluminum isopropoxide; the source of the silicon is tetraethyl orthosilicate; and the source of the cerium is cerium nitrate hexahydrate, cerium acetate, or cerium chloride.

11. A method of incorporating cerium into HZSM-5 to produce Catalyst 1 comprising: 1) preparing a dry gel of Si, Al, $H_2O$, and Ce, and (2) crystalizing the dry gel by steam assisted crystallization to form Catalyst 1.

12. The method according to claim 11 wherein the dry gel is prepared by combining Pluronic® F-127 or Pluronic® P-123 and de-ionized water at about 40° C.; followed adding the aluminum, silicon and cerium sources at about 40° C.; followed adding a structure directing agent tetrapropylammonium hydroxide, and mixing the resulting mixture in a reaction vessel at about 40° C.; followed aging the mixture at about 60° C. for at least about 8 hours; followed by exposing the reaction vessel to the atmosphere and raising the temperature to about 90° C. to dry the mixture until a dry solid gel is formed.

13. The method according to claim 12 wherein the dry gel is steamed at about 175° C. to form a powder; followed by washing and filtering the powder; and calcining the powder about 500° C. to about 600° C.

14. The method according to claim 11 wherein the source of aluminum is aluminum isopropoxide; the source of the silicon is tetraethyl orthosilicate; and the source of the cerium is cerium nitrate hexahydrate, cerium acetate or cerium chloride.

15. A process for the conversion biomass by catalytic fast pyrolysis, the process comprising heating the biomass to a conversion temperature in presence of the catalyst system of claim 1.

16. The process according to claim 15 wherein the conversion temperature ranges from about 500° C. to about 700° C.

17. The process according to claim 15 wherein the biomass is an oxygenated biomass feedstock.

18. The process according to claim 15 wherein the catalyst system selectively converts highly oxygenated biomass.

19. The process according to claim 18 wherein the highly oxygenated biomass is converted to organic compounds comprising furan, methylfuran, acetone and acetaldehyde.

20. A process for reducing coke formation during catalytic fast pyrolysis of biomass using HZSM-5, wherein the process comprises incorporating cerium into the HZSM-5 zeolite to produce Catalyst 1 prior to the catalytic fast pyrolysis.

* * * * *